United States Patent [19]
Sako

[11] Patent Number: 6,157,700
[45] Date of Patent: Dec. 5, 2000

[54] IMAGE READING APPARATUS

[75] Inventor: Tsukasa Sako, Utsunomiya, Japan

[73] Assignee: Canon Kabushiki Kaisha, Tokyo, Japan

[21] Appl. No.: 09/219,894

[22] Filed: Dec. 24, 1998

[30] Foreign Application Priority Data

Dec. 29, 1997 [JP] Japan ..................... 9-369399
Jan. 19, 1998 [JP] Japan ................... 10-021472
Dec. 18, 1998 [JP] Japan ................... 10-375983

[51] Int. Cl.$^7$ ................................. G03B 42/02
[52] U.S. Cl. .................. 378/98.12; 378/154; 382/128
[58] Field of Search ........................ 378/98.12, 154, 378/207; 382/128, 130, 132

[56] References Cited

U.S. PATENT DOCUMENTS 4,829,552  5/1989  Rossi et al. ........................ 378/154
5,050,198  9/1991  Honda ................................ 378/99
5,526,442  6/1996  Baba et al. ....................... 382/132
6,052,487  4/2000  Ito ............................. 382/128 X

FOREIGN PATENT DOCUMENTS

2-237277  9/1990  Japan .

Primary Examiner—David P. Porta
Attorney, Agent, or Firm—Fitzpatrick, Cella, Harper & Scinto

[57] ABSTRACT

After gain correction acquisition images are collected, an image reading apparatus calculates any deviation between the grid direction and the pixel line-up direction of a solid-state imaging element (12) in the rotation direction in the grid direction calculation process, and the deviation of a grid (11) in the rotation direction is corrected by accurately aligning the grid direction in the gain correction acquisition image to have a given relationship with respect to the pixel line-up direction, thus photographing an image in practice.

10 Claims, 8 Drawing Sheets

CALCULATION REGION

IMAGE READING APPARATUS

BACKGROUND OF THE INVENTION

The present invention especially relates to an image reading apparatus for imaging and reading an X-ray radiation distribution. In a conventional radiography apparatus, radiation is emitted by a radiation source toward an object as a medium to be inspected, and is intensity-modulated and scattered by the interaction between the radiation and object in correspondence with the internal structure of the object, thus forming a radiation image on a solid-state imaging element. At this time, in order to remove scattered radiation and to improve the contrast of the radiation image, a grid is placed in front of the solid-state imaging element to photograph an image.

On the other hand, an apparatus which takes correction photographs under various photographing conditions in advance, and corrects each photographed image using an image correction-photographed under a condition closest to the actual photographing condition is disclosed in Japanese Laid-Open Patent No. 2-237277.

However, the conventional apparatus does not consider the directivity of the grid placed between the solid-state imaging element and object. When an image is photographed via the grid by a method using a two-dimensional low-pass filter, if the grid direction is not taken into consideration, a problem is posed when the relative positional relationship between the grid and solid-state imaging element deviates. More specifically, when the grid is inserted, if gain correction coefficient data as a variation distribution of conversion efficiency is calculated using the two-dimensional low-pass filter, the calculated data contains unwanted data output from the grid.

Figure 8:
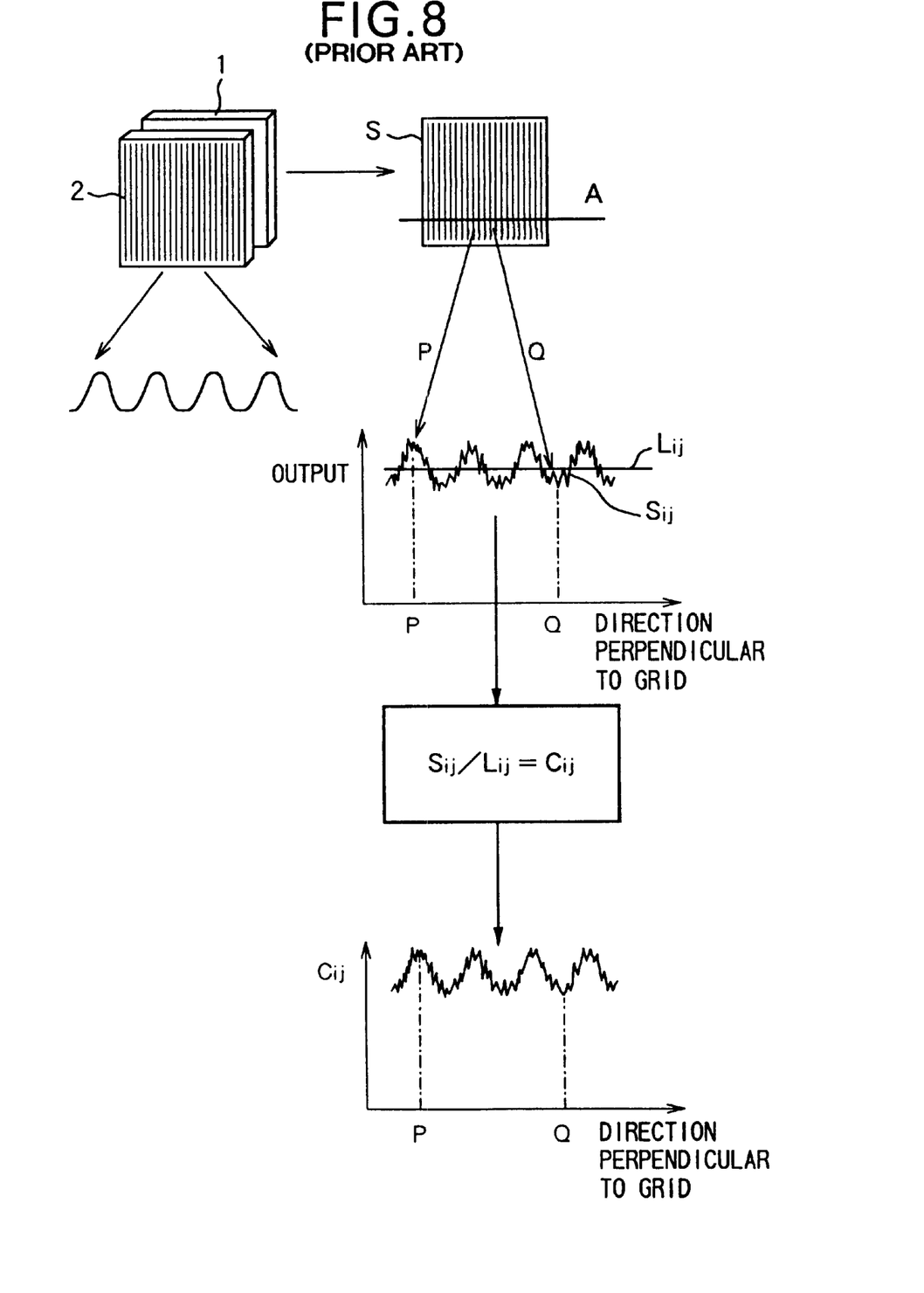
FIG. 8 is an explanatory view of the conventional gain correction coefficient generation process.

FIG. 8 shows a graph of a sensor output Sij and low-pass filter output Lij in a section A for a correction data acquisition image obtained by photographing in the absence of any object so as to obtain gain correction coefficient data. If the quotient obtained by dividing the sensor output Sij by the low-pass filter output Lij is used as gain correction coefficient data (Cij) that indicates the conversion efficiency of a solid-state imaging element 1, the gain correction coefficient Cij contains the influence of a grid 2.

More specifically, since the low-pass filter output Lij underestimates the X-ray dose contributed by the low-pass filter, a point P corresponding to a plus peak of the sensor output Sij exhibits higher apparent conversion efficiency than that of the solid-state imaging element 1 at the actual point P, and a point Q corresponding to a minus peak of the sensor output Sij exhibits lower apparent conversion efficiency than that of the solid-state imaging element 1 at the actual point Q. In this way, when the relative positional relationship between the grid 2 and sensor deviates upon photographing an actual object, the outputs can no longer correspond to the gain correction coefficient Cij. On the other hand, a calculation is made under the assumption that the relative positional relationship between the grid 2 and sensor has one-to-one correspondence with gain correction coefficient data. So, an image corrected using such gain correction coefficient data cannot be corrected accurately.

When gain correction is done in units of pixels of the solid-state imaging element 1, gain correction coefficient data for such correction is required upon photographing. However, when the relative positional relationship between the solid-state imaging element 1 and grid 2 upon collecting data in image acquisition deviates from that upon actually photographing an object, accurate correction cannot be attained.

Normally, as the X-ray technician takes it for granted that the solid-state imaging element 1 and grid 2 are always parallel to each other, the relative positional relationship between the solid-state imaging element 1 and grid 2 must always be automatically adjusted in a desired direction before or upon obtaining gain correction coefficient data. At this time, in order to assure more versatile use of the apparatus, accurate gain correction coefficient data must be obtained after not only the solid-state imaging element 1 and the grid 2 are adjusted in the pixel line-up direction, but also they are finely adjusted in respect to a direction perpendicular to the pixel line-up direction and other directions.

In Japanese Laid-Open Patent No. 5-237277 above, since photographing for correction must be done under a plurality of different photographing conditions, a storage memory requires a very large capacity.

SUMMARY OF THE INVENTION

It is an object of the present invention to provide an image reading apparatus which can solve the aforementioned problems, can perform photographing taking into account or decreasing the influence of any deviation between the direction of a grid and the pixel line-up direction of a solid-state imaging element, especially the deviation in the rotation direction.

In order to achieve the above object, an image reading apparatus according to the present invention comprises the following arrangement.

That is, there is provided an image reading apparatus for reading an intensity distribution of radiation that has been transmitted through an object to be inspected and a scattered ray removal grid, as image information using an imaging element having a plurality of pixels, comprising grid image acquisition means for obtaining a radiation intensity distribution via the scattered ray removal grid in the absence of the object to be inspected using the imaging element, and pattern detection means for detecting a pattern derived from the scattered ray removal grid from information of the radiation intensity distribution obtained by the grid image acquisition means.

Also, there is provided an image reading apparatus for reading an intensity distribution of radiation that has been transmitted through an object to be inspected and a scattered ray removal grid, as image information using an imaging element having a plurality of pixels, comprising initialization image reading means for obtaining a radiation intensity distribution as initialization image information via the scattered ray removal grid in the absence of the object to be inspected using the imaging element, pattern detection means for detecting a pattern derived from the scattered ray removal grid from the initialization image information, low-pass filter generation means for generating a low-pass filter on the basis of a detection result of the pattern detection means, and correction coefficient calculation means for calculating a correction coefficient used for correcting a conversion efficiency variation of the imaging element on the basis of image information obtained by filtering the initialization image information by the low-pass filter generated by the low-pass filter generation means, and the initialization image information.

Furthermore, there is provided an image reading apparatus for reading an intensity distribution of radiation that has been transmitted through an object to be inspected and a scattered ray removal grid, as image information using an imaging element having a plurality of pixels, comprising storage means for storing a radiation intensity distribution obtained in the absence of the object to be inspected using the grid and imaging element as initialization image information, and signal processing means for generating a low-pas filter based on a pattern derived from the grid from the initialization image information stored in the storage means, and obtaining gain correction information for each pixel of the imaging element by processing the initialization image information using the low-pass filter.

Moreover, there is provided an image reading apparatus for reading an intensity distribution of radiation that has been transmitted through an object to be inspected and a scattered ray removal grid, as image information using an imaging element having a plurality of pixels, comprising initialization image reading means for obtaining a radiation intensity distribution as initialization image information via the scattered ray removal grid in the absence of the object to be inspected using the imaging element, pattern detection means for detecting a pattern derived from the scattered ray removal grid from the initialization image information, and scattered ray removal grid displacement means for displacing the scattered ray removal grid on the basis of an output result of the pattern detection means.

According to a preferred aspect of the present invention, in the image reading apparatus according to claim 1, the pattern detection means has a function of obtaining information that pertains to a direction of the scattered ray removal grid on the basis of the radiation intensity distribution obtained by the grid image acquisition means.

According to a preferred aspect of the present invention, in the image reading apparatus according to claim 2, the information pertains to relative positional and angular deviations between the scattered ray removal grid and the grid image acquisition means.

According to a preferred aspect of the present invention, in the image reading apparatus according to claim 4, the correction coefficient calculation means calculates the correction coefficient by dividing individual pixel values of the initialization image information by individual pixel values of the image information obtained by filtering the initialization image information by the low-pass filter.

According to a preferred aspect of the present invention, in the image reading apparatus according to claim 4, the pattern detection means comprises grid direction calculation means for obtaining accumulated pixel information in a predetermined direction within an image region upon detecting the pattern derived from the scattered ray removal grid, and calculating a direction that maximizes a standard deviation of the accumulated pixel information by changing a direction in which the accumulated pixel information is obtained, and grid frequency calculation means for calculating a grid frequency by calculating a Fourier transform of the accumulated pixel information in the direction.

According to a preferred aspect of the present invention, in the image reading apparatus according to claim 7, the radiation intensity distribution obtained via the object to be inspected using the grid and imaging element is correction-processed using the gain correction information.

According to a preferred aspect of the present invention, in the image reading apparatus according to claim 9, the scattered ray removal grid displacement means aligns the grid by displacing in a translation direction and rotation direction.

BRIEF DESCRIPTION OF THE DRAWINGS

The accompanying drawings, which are incorporated in and constitute a part of the specification, illustrate embodiments of the invention, and together with the description, serve to explain the principles of the invention.

DETAILED DESCRIPTION OF THE INVENTION

Preferred embodiments of the present invention will be described in detail in accordance with the accompanying drawings.

The present invention will be described in detail hereinafter on the basis of an embodiment illustrated in FIGS. 1 to 7 and FIG. 9.

Figure 1:
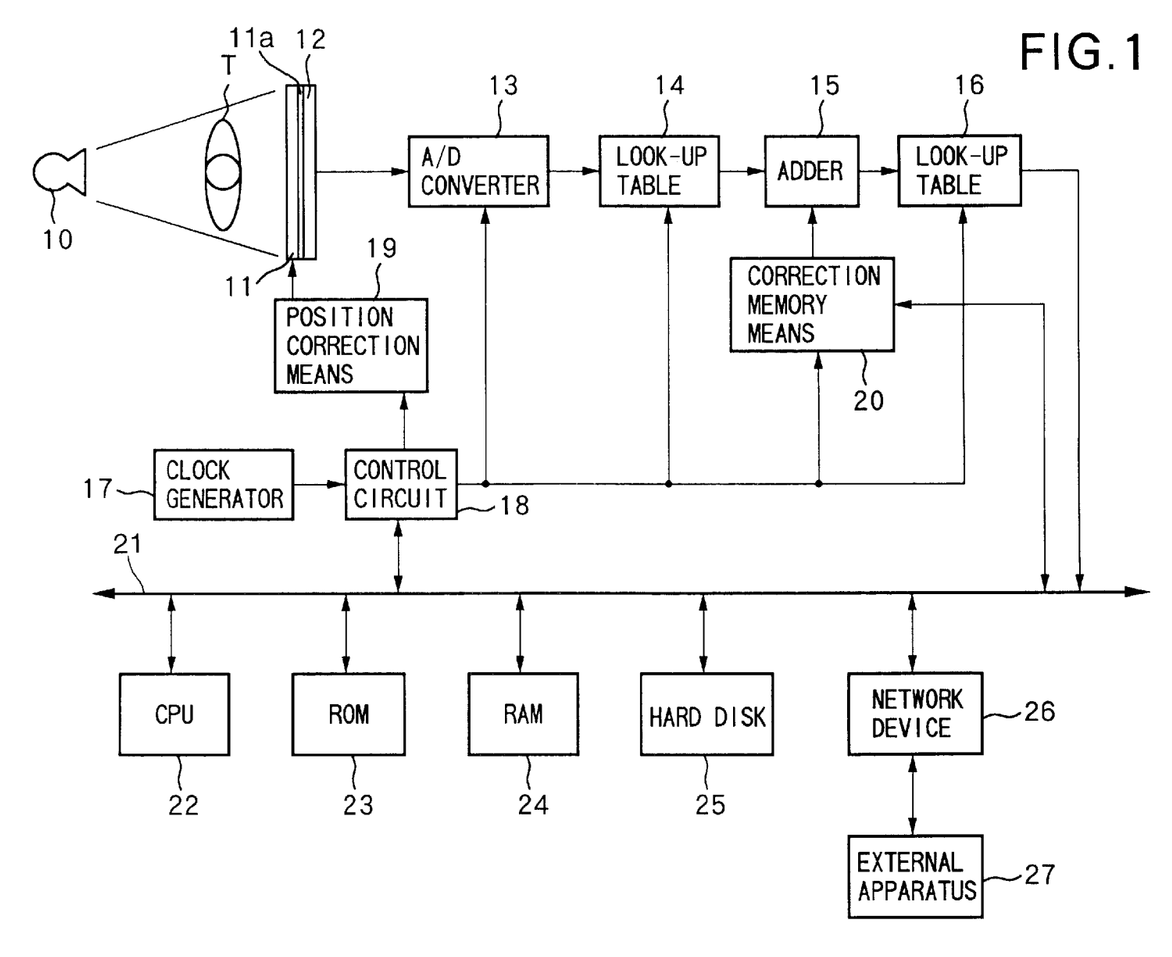
FIG. 1 is a block diagram showing the arrangement of an embodiment.

FIG. 1 is a block diagram showing the arrangement of an image reading apparatus of this embodiment. An object T is located between an X-ray generation means 10 and a solid-state imaging element 12 having a grid 11 and a scintillator 11a. The output from the solid-state imaging element 12 is connected in turn to an A/D converter 13, look-up table 14, adder 15, and look-up table 16. The output from a clock generator 17 is connected to a control circuit 18, the output of which is connected to the grid 11 via a position correction means 19. Also, the output of the control circuit 18 is connected to the adder 15 and look-up table 16 via the A/D converter 13, the look-up table 14, and a correction memory means 20.

The outputs of the look-up table 16, control circuit 18, and correction memory means 20 are connected to a bus 21, to which the outputs of a CPU 22, ROM 23, RAM 24, hard disk 25, and network device 26 are connected. The output of the network device 26 is connected to an external apparatus 27.

Figure 2:
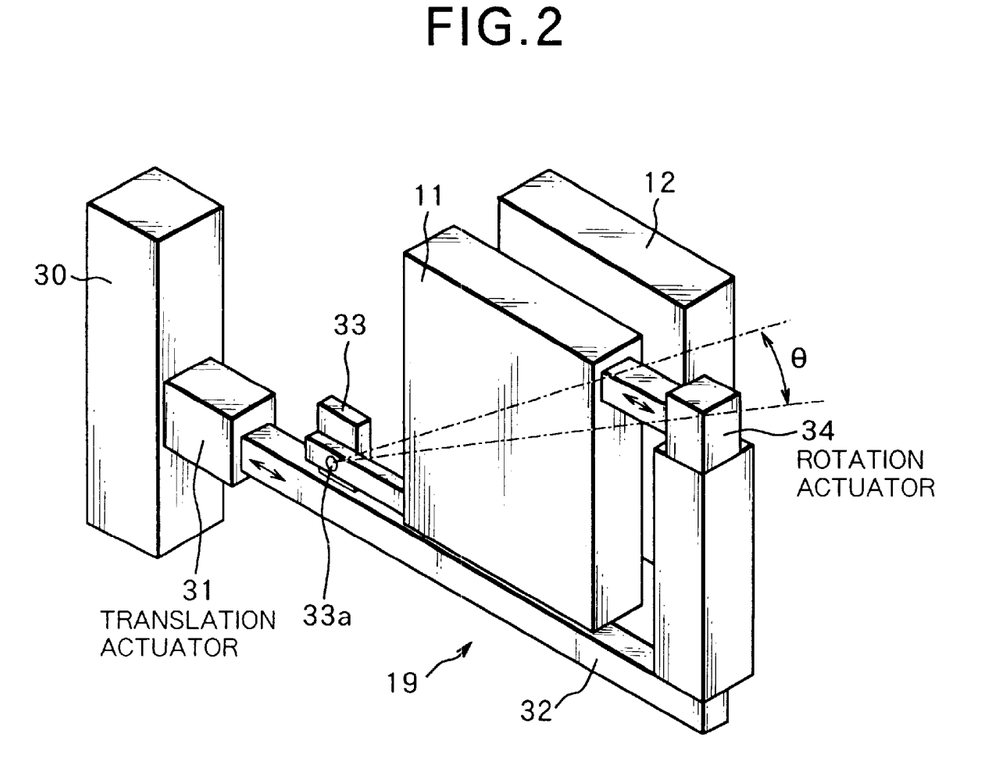
FIG. 2 is a perspective view of a position correction means.

FIG. 2 is a perspective view of the position correction means 19. A translation base 32 is located on the side surface of a base 30 via a translation actuator 31. A support member 33 and rotation actuator 34 are placed on the translation base 32. The grid 11 is rotatably supported by a fulcrum 33a provided to the support member 33 below its one side surface, and is attached to the rotation actuator 34 above the other side surface. The actuators 31 and 34 use solenoids, motors, piezoelectric elements, and the like to translate the grid 11 in the directions of an arrow B and to rotate it in the direction of an arrow θ in accordance with a signal from the control circuit 18, which is controlled by the CPU 22. The solid-state imaging element 12 is placed behind the grid 11.

The image reading apparatus has a function of calculating any deviation between the grid direction and the pixel line-up direction of the solid-state imaging element 12 from the gain correction acquisition images in the grid direction calculation process after gain correction acquisition images are obtained, and aligning the grid direction in the gain correction acquisition images by the position correction means 19. The CPU 22, ROM 23, RAM 24, and hard disk 25 control the entire system, and photographing is done in response to a command supplied from the CPU 22 to the control circuit 18. The control circuit 18 operates in synchronism with the output from the clock generator 17.

Correction data acquisition images are photographed before normal photographing. In the photographing sequence for obtaining correction data acquisition image data, the CPU 22 loads linear tables onto the look-up tables 14 and 16, and gives a value of all "0"s to the correction memory means 20. Data obtained by this method allows to collect a correction data acquisition image output from the A/D converter 13 as digital data. The correction data acquisition image data is used to calculate the gain correction coefficient using the method to be described below, and the calculated gain correction coefficient is stored in a nonvolatile medium such as a hard disk or the like.

Figure 3:
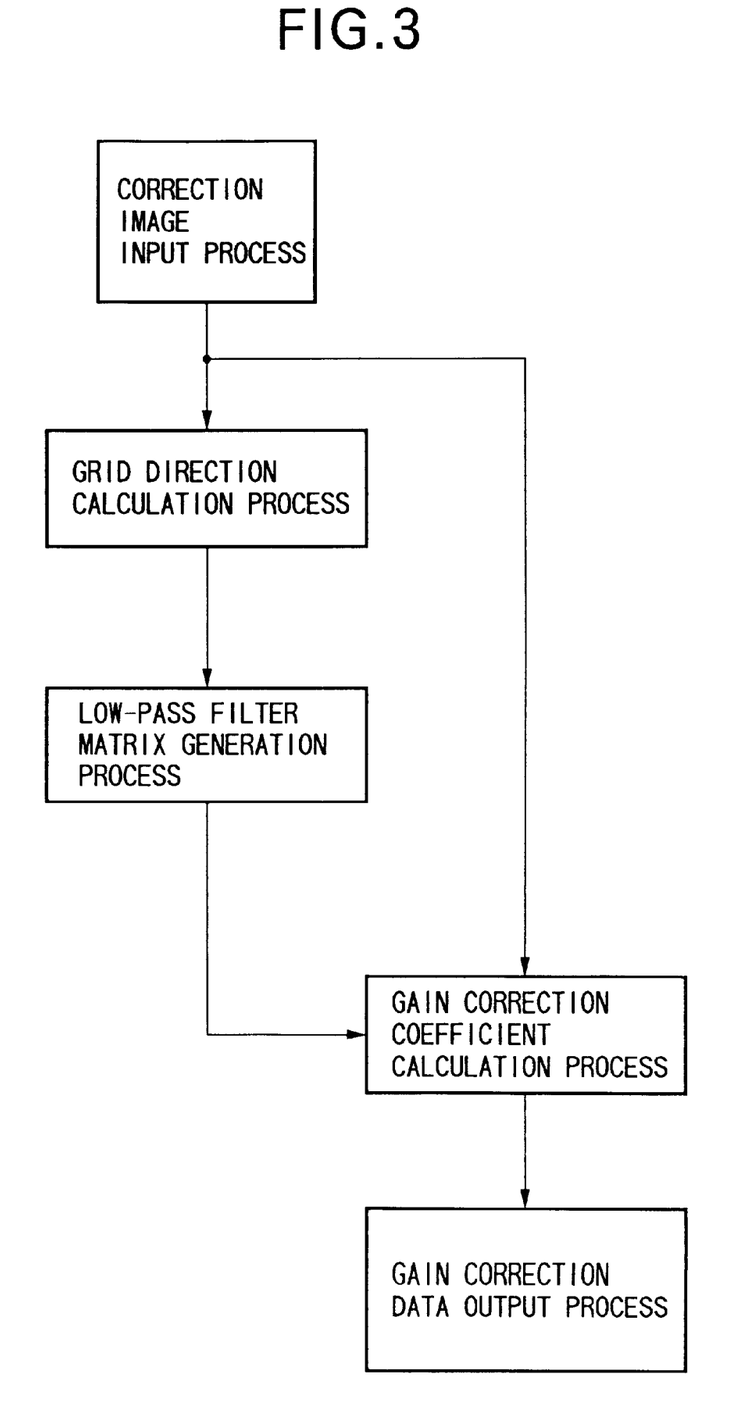
FIG. 3 is a chart for explaining the gain correction coefficient generation process.

FIG. 3 shows the process for generating gain correction data from the collected correction data acquisition images, and this generation process includes a grid direction calculation process, low-pass filter matrix generation process, and gain correction coefficient calculation process.

Figure 4:
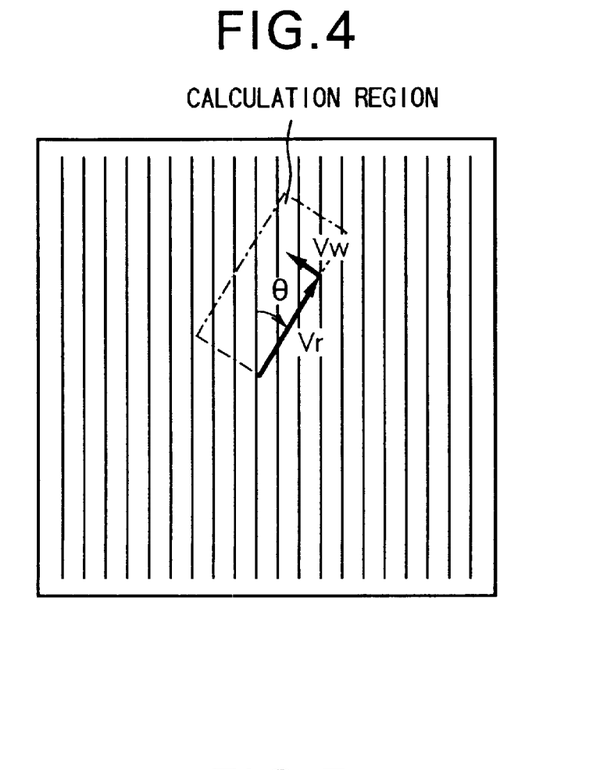
FIG. 4 is an explanatory view of the grid direction calculation process.

FIG. 4 is a view for explaining the processing in the grid direction calculation process. A vector V is calculated from a radius vector Vr and a vector Vw perpendicular to the radius vector Vr. The vector V is calculated by the equation below while changing the radius vector Vr as a function of a rotation angle $\theta$.

$$V = Vr + Vw$$

Hence, when the radius vector Vr changes according to $\theta$, the collection width vector Vw changes in correspondence with changes in Vr to maintain an orthogonal relationship.

The rotation angle $\theta$ is increased in 0.1-radian increments from 0 radian to 1 radian, and the absolute value |Vr| of the radius vector is changed from e.g., 0 to 32 by one pixel per increment. In each case, the absolute value |Vw| of the collection width vector is changed from, e.g., 0 to 64 by one pixel each time, and the pixel value of a pixel that approximates the position indicated by the vector V is calculated. By accumulating the pixel values in the direction Vr, 65 pieces of accumulated pixel information with a size |Vw| can be collected.

Figure 9:
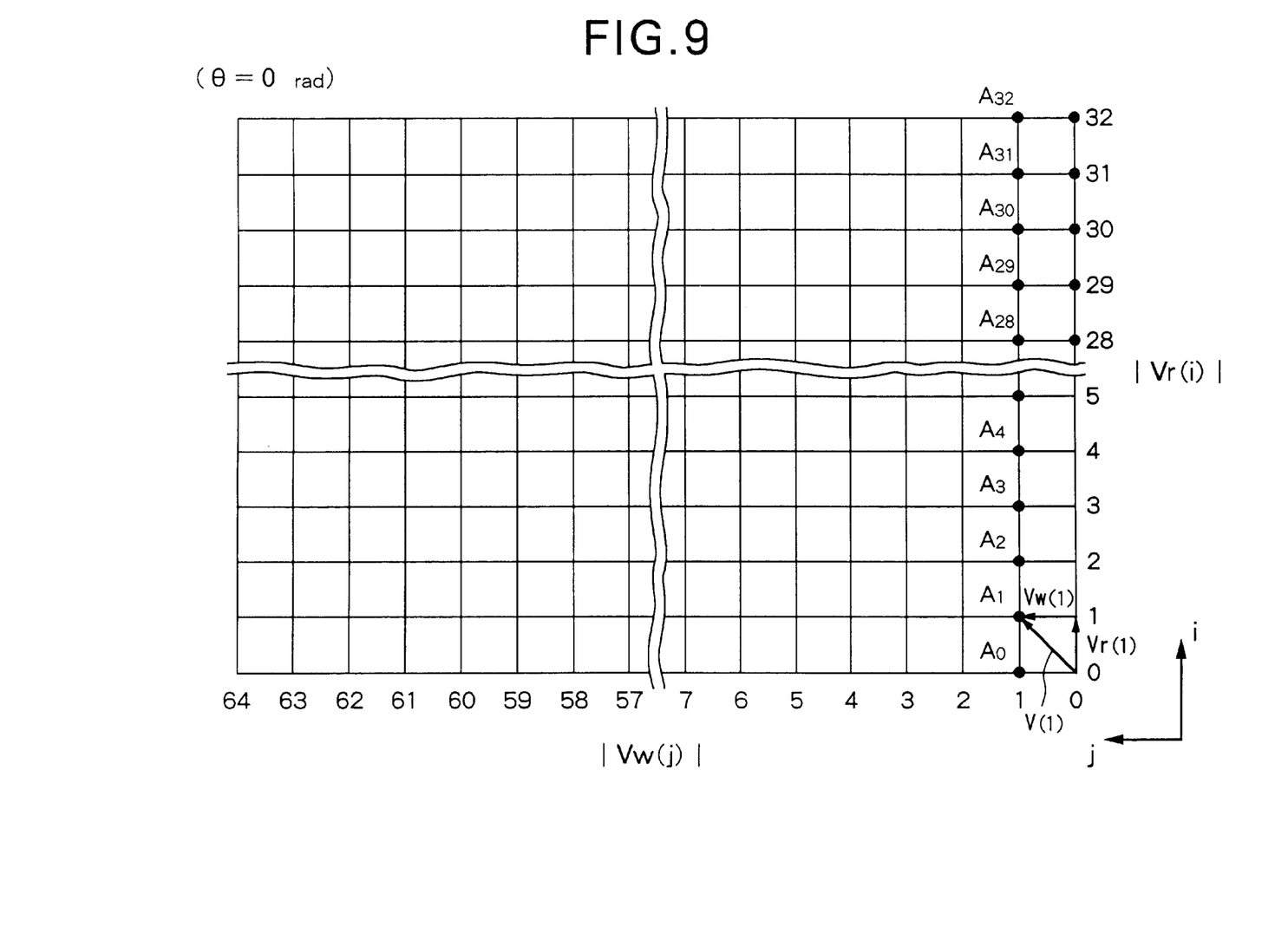
FIG. 9 is a graph showing the relationship between the position and pixel on the basis of the absolute value |Vr| of a radius vector and the absolute value |Vw| of a collection vector.

FIG. 9 shows a plane defined by the 0th to 32nd pixels (i direction) which are associated with |Vr|, and the 0th to 64th pixels (j direction) associated with |Vw| when the rotation angle I=0 radian (rad). Using the aforementioned relationship between the radius vector and collection width vector, a position vector that specifies the pixel position can be expressed as:

$$V(i, j) = Vr(i) + Vw(j)$$

If Aij represents the pixel value of a pixel corresponding to the position indicated by the vector V(i, j), if j=1, pixel values Ai1 (i=0 to 32) corresponding to pixels i=0 to 32 can be obtained on the basis of images corrected in the correction image input process shown in FIG. 3. Likewise, pixel values Aij (i=0 to 32, j=0 to 64) corresponding to all pixels j, i.e., j=0 to 64, can be obtained.

The angle in the grid direction is the one that gives a maximum standard deviation of the accumulated value of the pixel values. The accumulation assumes elements of a column having a variable parameter i while j is constant. For example, when j=1, the pixel values in the column direction are $A_0, A_1, A_2, A_3, \ldots, A_{32}$, and their accumulated value is $M(1, \theta) = A_0 \cdot A_1 \cdot A_2 \cdot A_3 \ldots A_{32}$.

In cases other than j=1, accumulated values (M(j, $\theta$) (j=0 to 64)) can be similarly calculated. The values of standard deviation D($\theta$) of the accumulated values M(j, $\theta$) from j=0 to j=64 at each rotation angle $\theta$ when the rotation angle $\theta$ is changed are obtained. A radian value $\theta_0$ that maximizes the standard deviation D($\theta$) defines the deviation angle of the grid direction with respect to the pixel line-up direction of the solid-state imaging element. By calculating Fourier transforms on the basis of 65 pieces of obtained image information at the rotation angle $\theta_0$, the frequency component of the grid 11 can be calculated. In other words, a wavelength range which is likely to be that of the grid 11 is designated in advance, and a wavelength $W_0$ corresponding to a maximum amplitude of Fourier transformed data is obtained from this range. Then, the wavelength $W_0$ of the grid 11 having a pixel of the solid-state imaging element 12 as one unit can be calculated.

Figure 5:
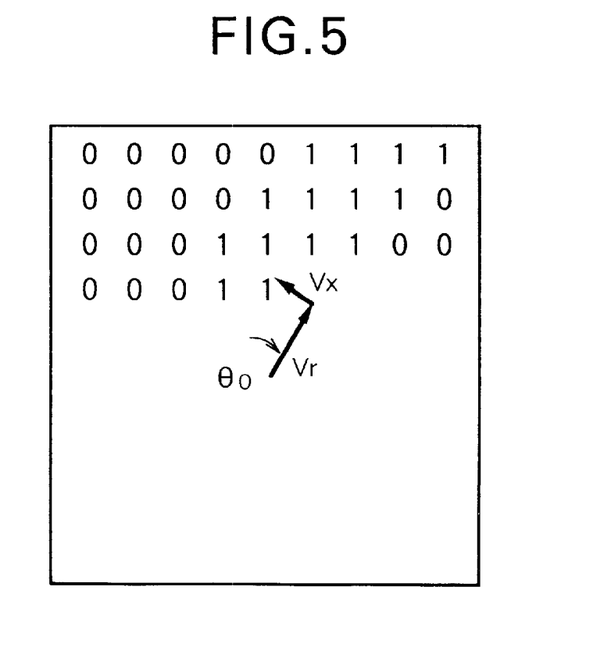
FIG. 5 is an explanatory view of the low-pass filter matrix calculation process.

FIG. 5 shows the process of generating a low-pass filter matrix using the radian value $\theta_0$ of the deviation angle and the wavelength $W_0$ of the grid 11. In this embodiment, a low-pass filter matrix is generated by varying vectors Vx and Vy with respect to the radian value $\theta_0$ obtained in the previous process. The vector Vx is changed so that Vx assumes a maximum absolute value at a size, for example, between $W_0/2$ half the wavelength $W_0$ of the grid 11 and $W_0/16$ one-sixteenth of the wavelength $W_0$, and 1 is recorded at a position indicated by the vector sum Vy+Vx in the matrix. Also, by changing the vector Vy to fill all the matrix positions with values, the low-pass filter matrix that extracts a region whose size is between a half and a one-sixteenth of the grid width along the grid direction can be generated. Data averaged by using the low-pass filter matrix is then divided by a number of "1" in the matrix.

Figure 6:
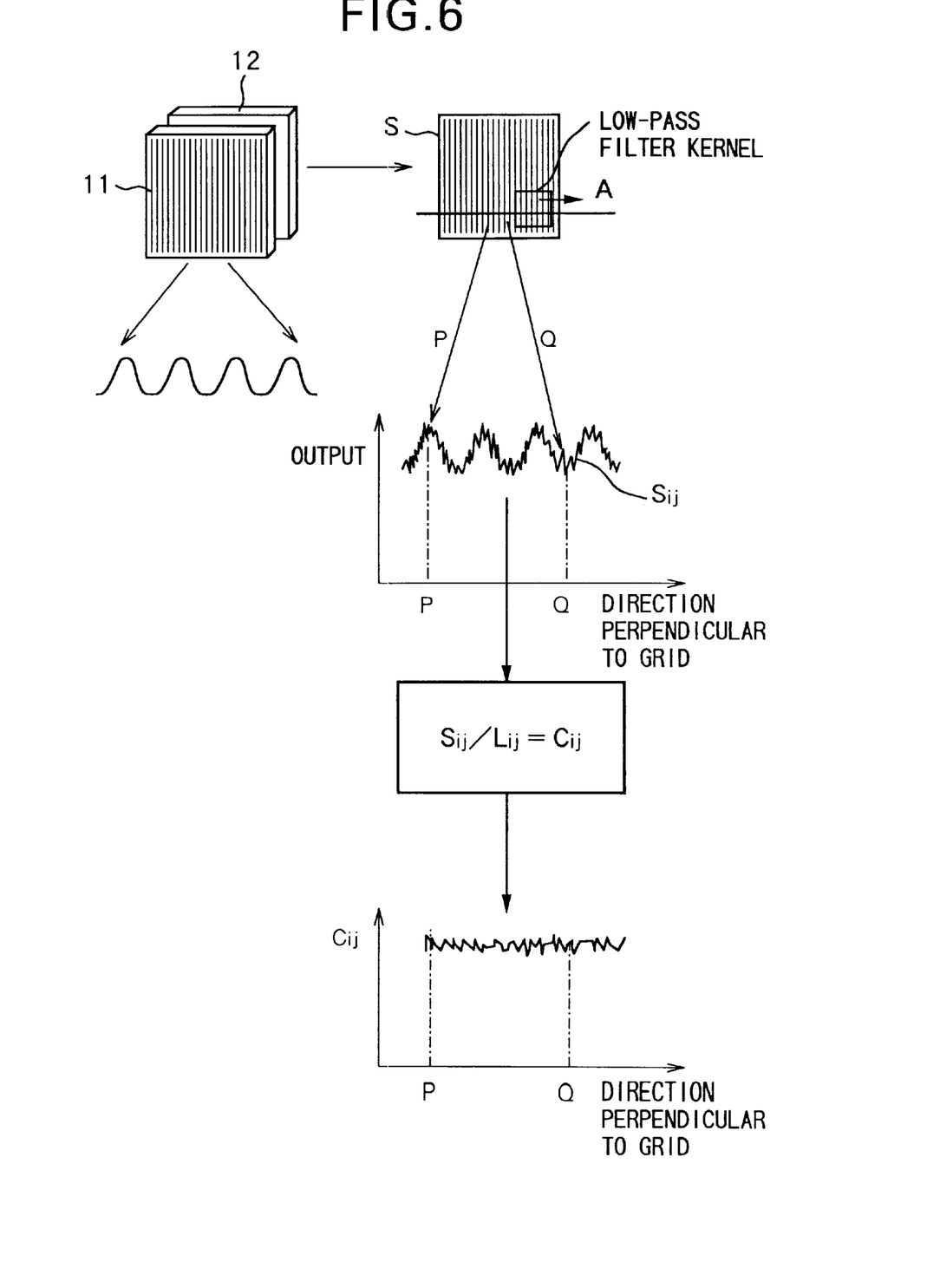
FIG. 6 is an explanatory view of gain correction coefficient generation free from any influences of a grid.

FIG. 6 is an explanatory view of the process for kernel-moving the low-pass filter matrix obtained in the previous process to a correction data acquisition image S while calculating it using a gain correction coefficient calculation formula:

$$Sij/Lij = Cij$$

where Sij represents the sensor output, Lij represents the low-pass output, and Cij represents the gain correction coefficient to be obtained.

In this embodiment, log(Cij) is calculated using logarithmic conversion by subtraction:

$$\log(Cij) = \log(Sij/Lij) = \log(Sij) - \log(Lij)$$

As shown in FIG. 6, since the low-pass filter output synchronizes the fluctuation in the sensor output caused by the existence of the grid 11 on subtracted from the gain correction coefficient Cij, no influence of the grid 11 appears. Hence, the gain correction coefficient log (Cij) is saved in the hard disk 25 or RAM 24, and is used in normal photographing later. In case of normal photographing, the object T is located between the X-ray generation means 10 and solid-state imaging element 12, a linear-logarithmic conversion table for converting a linear function into a logarithmic function is loaded onto the look-up table 14, and a logarithmic-linear conversion table for converting a logarithmic function into a linear function is loaded onto the look-up table 16. Then, the gain correction coefficient data log (Cij) calculated in this embodiment is supplied to the correction memory means 20 to calculate:

$$Oij = Iij/(Sij/Lij)$$

where Oij is the pixel value after gain correction, and Iij is the input pixel value.

To easily implement these calculations by hardware, in this embodiment, data, which is hardware-processed by logarithmic calculation and corrected with gain variations in units of pixels by the formula below, is output:

| log(Oij) | = | log (Iij/Sij/Lij) |
|---|---|---|
|  | = | log (Iij) - log (Sij/Lij) |
|  | = | log (Iij) - log (Cij) |

For the purpose of more accurately adjusting the relative positional relationship between the grid 11 and solid-state imaging element 12, this result is used in photographing. In this embodiment, since the influence of the grid 11 is not canceled from the finally output image, the technician or doctor can clearly observe the presence of the grid 11 on the image. At this time, since it is preferable that the direction of the grid 11 do not deviate from the pixel line-up direction of the solid-state imaging element 12, the relative positional relationship between the grid 11 and solid-state imaging element 12 is controlled to agree with the direction set by the user, thus accurately finely adjusting the grid direction the user desired, in this embodiment.

Figure 7:
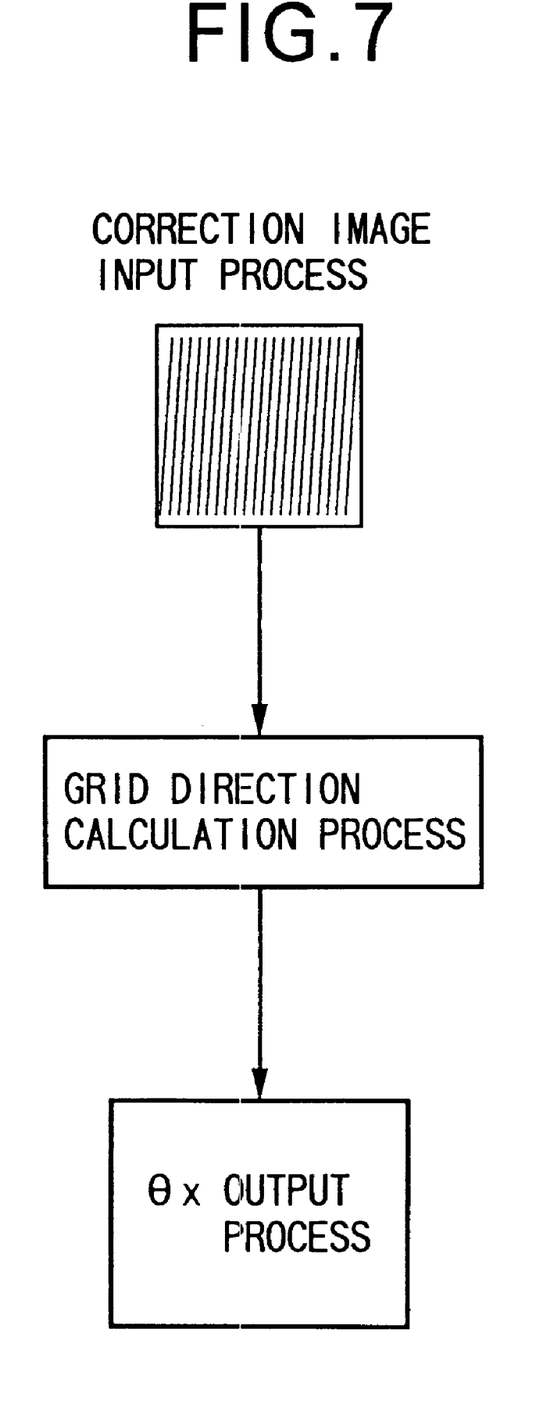
FIG. 7 is a chart for explaining the grid direction calculation process.

FIG. 7 shows the process for calculating an angle value $\theta x$ the grid 11 makes with the solid-state imaging element 12 upon gain correction by a similar method. A difference $\Delta$ between this value $\theta x$ and a grid direction $\theta u$ designated by the user is calculated by $\Delta = \theta x - \theta u$, and is supplied to the position correction means 19. The CPU 22 converts the input rotation angle $\Delta$ into an angular change caused by actuation of the rotation actuator 34 by an appropriate conversion function $\theta a = f(\Delta)$, and controls the rotation actuator 34 using the converted angle. On the other hand, the translation actuator 31 is used for finely adjusting the entire grid 11 in the right-and-left direction. In this way, the grid direction can be accurately finely adjusted to agree with the direction designated by the user. In the above embodiment, even when the positional relationship between the grid 11 and solid-state imaging element 12 is free from any variation, a similar problem is posed if the relative positional relationship among the X-ray generation means 10, solid-state imaging element 12, and grid 11 varies. However, the present invention can solve this problem. Even when the relative positional relationship among the X-ray generation means 10, solid-state imaging element 12, and grid 11 has varied, since accurate correction can be attained, an image can be photographed by correcting gains in units of pixels of the solid-state imaging element. Therefore, the doctor or technician who observes the image is free from any moire image, and the storage memory need only have a small capacity for storing gain correction coefficient data alone. Furthermore, the relative positional relationship can be positively varied, and the user can align the grid direction to have a given relationship with respect to the pixel line-up direction of the solid-state imaging element. Hence, the technician or doctor can refer to an image in the accurately aligned grid direction.

The present invention is not limited to the above embodiments and various changes and modifications can be made within the spirit and scope of the present invention. Therefore, to appraise the public of the scope of the present invention, the following claims are made.

What is claimed is:

1. An image reading apparatus for reading an intensity distribution of radiation that has been transmitted through an object to be inspected and a scattered ray removal grid, as image information using an imaging element having a plurality of pixels, comprising:

grid image acquisition means for obtaining a radiation intensity distribution via said scattered ray removal grid in the absence of the object to be inspected using said imaging element; and pattern detection means for detecting a pattern derived from said scattered ray removal grid from information of the radiation intensity distribution obtained by said grid image acquisition means.

2. The apparatus according to claim 1, wherein said pattern detection means has a function of obtaining information that pertains to a direction of said scattered ray removal grid on the basis of the radiation intensity distribution obtained by said grid image acquisition means.

3. The apparatus according to claim 2, wherein the information pertains to relative positional and angular deviations between said scattered ray removal grid and said grid image acquisition means.

4. An image reading apparatus for reading an intensity distribution of radiation that has been transmitted through an object to be inspected and a scattered ray removal grid, as image information using an imaging element having a plurality of pixels, comprising:

initialization image reading means for obtaining a radiation intensity distribution as initialization image information via said scattered ray removal grid in the absence of the object to be inspected using said imaging element;

pattern detection means for detecting a pattern derived from said scattered ray removal grid from the initialization image information;

low-pass filter generation means for generating a low-pass filter on the basis of a detection result of said pattern detection means; and correction coefficient calculation means for calculating a correction coefficient used for correcting a conversion efficiency variation of said imaging element on the basis of image information obtained by filtering the initialization image information by the low-pass filter generated by said low-pass filter generation means, and the initialization image information.

5. The apparatus according to claim 4, wherein said correction coefficient calculation means calculates the correction coefficient by dividing individual pixel values of the initialization image information by individual pixel values of the image information obtained by filtering the initialization image information by the low-pass filter.

6. The apparatus according to claim 4, wherein said pattern detection means comprises:

grid direction calculation means for obtaining accumulated pixel information in a predetermined direction within an image region upon detecting the pattern derived from said scattered ray removal grid, and calculating a direction that maximizes a standard deviation of the accumulated pixel information by changing a direction in which the accumulated pixel information is obtained; and grid frequency calculation means for calculating a grid frequency by calculating a Fourier transform of the accumulated pixel information in the direction.

7. An image reading apparatus for reading an intensity distribution of radiation that has been transmitted through an object to be inspected and a scattered ray removal grid, as image information using an imaging element having a plurality of pixels, comprising:

storage means for storing a radiation intensity distribution obtained in the absence of the object to be inspected using said grid and imaging element as initialization image information; and signal processing means for generating a low-pass filter based on a pattern derived from said grid from the initialization image information stored in said storage means, and obtaining gain correction information for each pixel of said imaging element by processing the initialization image information using the low-pass filter.

8. The apparatus according to claim 7, wherein the radiation intensity distribution obtained via the object to be inspected using said grid and imaging element is correction-processed using the gain correction information.

9. An image reading apparatus for reading an intensity distribution of radiation that has been transmitted through an object to be inspected and a scattered ray removal grid, as image information using an imaging element having a plurality of pixels, comprising:

initialization image reading means for obtaining a radiation intensity distribution as initialization image information via said scattered ray removal grid in the absence of the object to be inspected using said imaging element;

pattern detection means for detecting a pattern derived from said scattered ray removal grid from the initialization image information; and scattered ray removal grid displacement means for displacing said scattered ray removal grid on the basis of an output result of said pattern detection means.

10. The apparatus according to claim 9, wherein said scattered ray removal grid displacement means aligns said grid by displacing in a translation direction and rotation direction.

* * * * *